United States Patent
Bobson et al.

(10) Patent No.: US 9,604,248 B2
(45) Date of Patent: Mar. 28, 2017

(54) REMOVING A SOLVENT FROM A DRUG-ELUTING COATING

(71) Applicant: Abbott Cardiovascular Systems Inc., Santa Clara, CA (US)

(72) Inventors: Charles R. Bobson, San Mateo, CA (US); Kurt Scheinpflug, San Jose, CA (US); Yung-Ming Chen, San Jose, CA (US); Jeff H. Smith, Redwood City, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 240 days.

(21) Appl. No.: 14/302,326

(22) Filed: Jun. 11, 2014

(65) Prior Publication Data

US 2014/0338214 A1    Nov. 20, 2014

Related U.S. Application Data

(63) Continuation of application No. 12/497,133, filed on Jul. 2, 2009, now Pat. No. 8,795,761.

(51) Int. Cl.
*B05D 3/00* (2006.01)
*F26B 21/00* (2006.01)
*A61F 2/82* (2013.01)

(52) U.S. Cl.
CPC ............... *B05D 3/007* (2013.01); *A61F 2/82* (2013.01); *F26B 21/004* (2013.01); *A61F 2240/002* (2013.01)

(58) Field of Classification Search
CPC .... B05D 3/007; F26B 21/006; B05B 13/0242
USPC .... 427/2.1, 2.24, 372.2; 118/58, 63; 34/381, 34/442, 104
See application file for complete search history.

(56) References Cited

U.S. PATENT DOCUMENTS

| | | | |
|---|---|---|---|
| 5,879,697 A | 3/1999 | Ding et al. | |
| 7,504,125 B1 * | 3/2009 | Pacetti | A61L 31/16 427/2.24 |
| 2008/0044675 A1 | 2/2008 | Ding et al. | |

FOREIGN PATENT DOCUMENTS

GB           1024671 A  *  3/1966  ............ F26B 21/004

\* cited by examiner

*Primary Examiner* — Cachet Sellman
(74) *Attorney, Agent, or Firm* — Squire Patton Boggs (US) LLP

(57) ABSTRACT

A coating device for coating a medical device with a drug-eluting material uses an in-process drying station between coats to improve a drug release profile. The drying station includes a heat nozzle configured for applying a uniform drying gas.

9 Claims, 10 Drawing Sheets

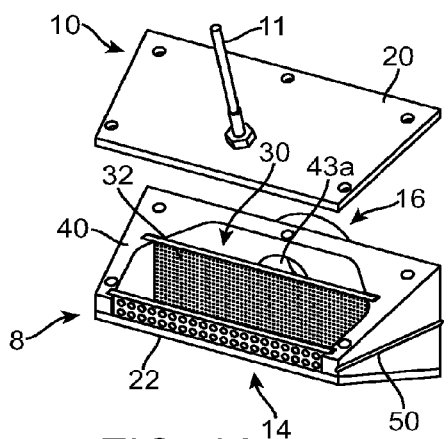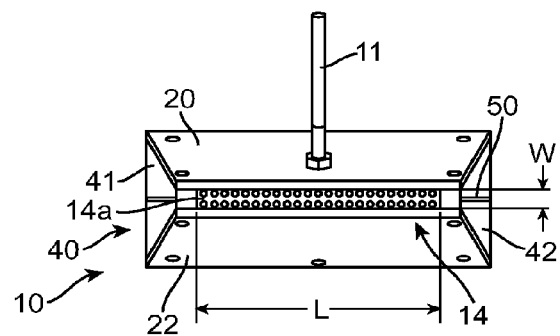
FIG. 1A  FIG. 1B
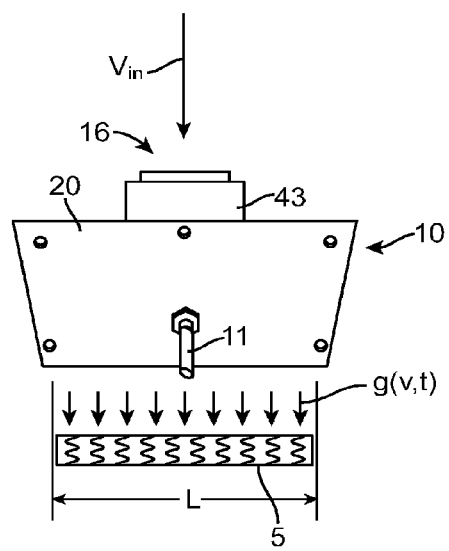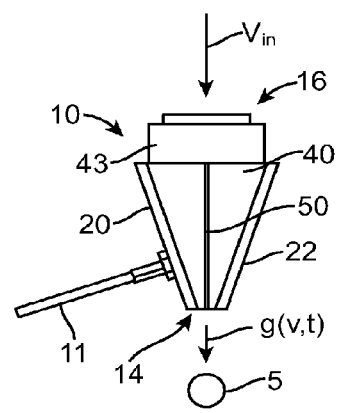
FIG. 2A  FIG. 2B

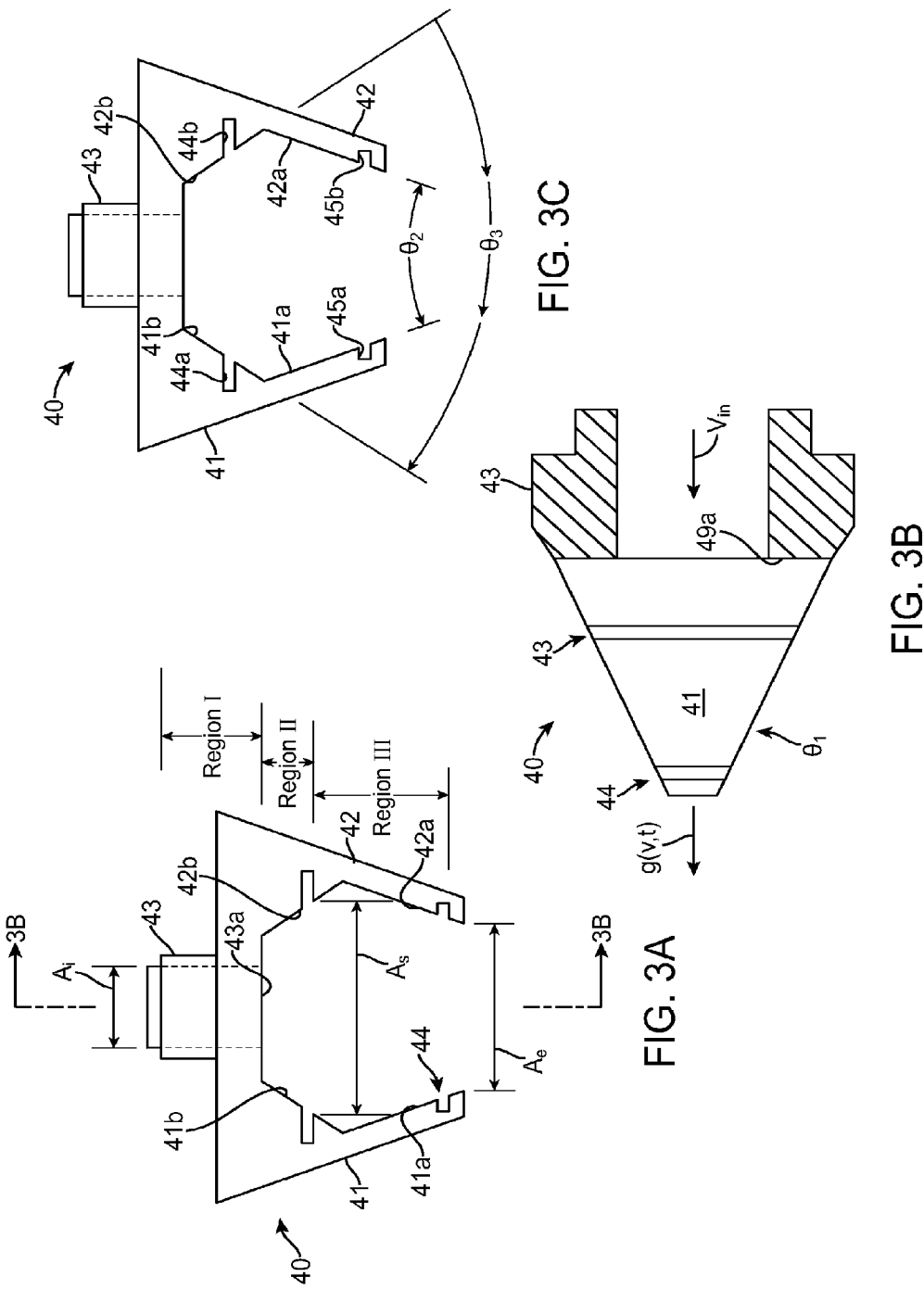

REMOVING A SOLVENT FROM A DRUG-ELUTING COATING

This application is a continuation of U.S. patent application Ser. No. 12/497,133 (now U.S. Pat. No. 8,795,761), filed Jul. 2, 2009.

BACKGROUND OF THE INVENTION

Field of the Invention

The present invention relates to drug-eluting medical devices; more particularly, this invention relates to processes for controlling the interaction among polymer, drug and solvent, and the release rate of a drug for drug eluting medical devices.

Background of the Invention

Strict pharmacological and good mechanical integrity of a drug eluting medical device are required to assure a controlled drug release. Significant technical challenges exist when developing an effective and versatile coating for a drug eluting medical device, such as a stent.

A coating may be applied by a spray coating process. A drug-polymer composition dissolved in a solvent is applied to the surface of a medical device using this method. The amount of drug-polymer to be applied has been expressed as a target coating weight, which corresponds to the weight of the coating after a substantial amount of the solvent has been removed.

It is desirable to obtain better control over the drug-eluting product. Specifically, there is a need to better control the rate of release of a drug, or the effectiveness of a drug when released from the coating. To date the known prior art has failed to provide adequate solutions.

SUMMARY OF THE INVENTION

The invention improves on the art by providing an apparatus and method for forming a drug-eluting coating that offers greater control over the release rate for a drug and less undesired interaction between a carrier solvent and the drug-polymer matrix. According to the embodiments, a spray nozzle is used to apply the coating material. And a heat nozzle is used to apply inter-pass drying of coating. The term "inter-pass drying" means drying, or removing solvent between one, two, three or more spray passes. The weight of material per coat is extremely light, about 2% of the total coating weight according to one embodiment. This means, for this particular embodiment, 50 spray passes are needed to reach 100% of the coating weight.

Previous efforts to produce a more consistent and stable drug release profile have not been entirely satisfactory. A more precise, controllable/predictable release rate is sought. Efforts to improve upon the controllability and consistency of the release rate of the drug have focused on the structure of the polymer, type or structure of the polymer, and the type of solvent used. However, these improvements have not been able to satisfactorily meet the needs for certain clinical applications, or provide a morphology that can be widely used.

A "drug release profile", or "release profile" means the morphology, or characteristics of a drug-eluting matrix that delivers an expected therapeutic behavior after being placed within a body. A drug release profile, or release profile therefore informs one of such things as the predictability of the release rate, variation, if any, in the release rate over time or on a per unit area basis across a drug-eluting surface.

It has been discovered that a significant improvement in the ability to tailor a drug release profile to suit a particular objective such as producing a specific release rate, uniformity in the release rate over a drug eluting surface, and/or uniformity in a production setting (high throughput) lay in obtaining more precise control over the amount of solvent present, or rate of solvent removal. The criticality of solvent removal, distribution, etc. generally depends on the drug-polymer-solvent formulation and particular objectives sought. While it is known that the morphology of a drug-polymer matrix is influenced by the presence of a solvent, it was discovered that this interaction played a more significant role than previously thought. Based on this conclusion, a more effective process for controlling the amount of solvent-polymer-drug interaction was sought. It was found that the coating weight per spray cycle and manner in which solvent was removed, in connection with the coating thickness was an important consideration.

A relatively high coating weight per spray cycle has been sought in the past, because this minimizes processes time and increases throughput. Maintaining control over the amount or rate of solvent removal is, however, challenging unless an applied coating layer is relatively thin. If the applied layer is too thick the resistance of the solvent to removal quickly becomes non-linear and therefore less easy to control or predict. When the solvent is removed from a thick layer, therefore, the potential for undesired interaction among the solvent, polymer and drug, and related problems begin to impair the ability to retain control over the release profile.

The biocompatibility of the polymer used for a drug eluting medical device, e.g., a stent, is essential. The polymer must be non-inflammatory, capable of being expanded without flaking or delaminating from the stent, and be able to control the drug release at a predictable rate. Very few polymer systems can meet the requirements. Preferably, EVAL is chosen as a drug matrix material for drug eluting stents. It has shown favorable biological responses. EVAL is a semi-crystalline random copolymer and it is hygroscopic due to its hydroxyl group. The percentage crystallinity of EVAL coating on the stent is dependent on the process conditions (process temperature, humidity, or residual solvent). A solvent (DMAc or DMSO) used to dissolve EVAL has a high boiling point. As such, the solvent must be actively removed from the coating, e.g., by heating.

Process conditions can affect the desired morphology. For example, if there is excess residual solvent, i.e., solvent not removed between or after a spray cycle, the solvent can induce a plasticizing effect, which can significantly alter the release rate. Therefore, it can be critically important to have a process that produces a coating with consistent properties—crystallinity, % solvent residue, % moisture content, etc. If one or more of these parameters are not properly controlled, such that it varies over the thickness or across a surface of a drug-eluting device, then the release profile is affected. One or more of these considerations can be more critical for some drug-polymer-solvent formulations than for other formulations.

To facilitate the incorporation of a drug on a stent, spraying a low solid percent polymer/drug solution over the stent followed by removing the solvent has become feasible in controlling the amount of drug (in micrograms range) deposited on the stent and the release profile. It has now been discovered that a good coating quality benefits from using this spray technique, i.e., properties such as the crystallinity, % solvent residue, and % moisture content are more controllable as the coating weight is built up over several applied coatings. However, a stent having tight geometry (to minimize the crimped stent OD size) adds significant technical challenges to this method. There is a need to remove at least some of the solvent, in an efficient, predictable manner between spray cycles (a spray cycle may include one or more spray passes, e.g., passing a spray nozzle lengthwise over a rotating stent). In a preferred embodiment, a spray cycle includes one, two, three or more passes in order to obtain a 2% coating weight in a spray cycle. Ideally one would want to remove all solvent after each coating. It will be readily understood, however, that this is not a practical solution. Accordingly, removing all solvent between each spray cycle does not address the need in the art.

Studies of the drying effect on drug release (EVAL-drug system) indicated an immediate need for an in-process drying technique to remove a solvent on the coated stent after each spray cycle. This is a critical step in producing more stable products while retaining a high throughput.

The properties of a solvent, e.g., surface tension, vapor pressure or boiling point, viscosity, and dielectric constant, used in dissolving a polymer have a dominant effect on the coating quality, coating process throughput, drug stability, and the equipment required to process it. A solvent can, of course, be removed by applying a heated gas over the stent. Surprisingly and unexpectedly, however, it was found that this drying step must be carefully controlled in order to achieve the desired end result. A uniform and efficient heat transfer from the gas to the coating surface must also take place.

The evaporation rate of a suitable solvent has an inverse relationship with the coating thickness (generally inversely proportional to the thickness) for a thin film coating. And the resistance increases non-linearly as the coating thickness increases. As alluded to earlier, this non-linearity should be avoided. When the thickness is within the linear range higher efficiency, uniformity and more control is achieved when removing the solvent. As a result, a more consistent drug release profile is obtained because there is the least drug-solvent-polymer interaction, solvent plasticizing and extracting of the drug. It is therefore desired to achieve more control over, not only the uniformity of properties across the thickness, but also the ability to remove solvent. This is because residual solvent on the drug eluting stent may induce adverse biological responses, compromise coating properties, induce drug degradation, and alter release profile. The ratio polymer-to-drug applied during each spray cycle can be 1:1, 2:1, 3:1, 4:1 or 5:1.

Thus, it has found that a release rate can be better controlled by applying many coats of a low percentage solution, e.g., 2% of the final coating weight, with a drying step between each spray cycle. Thus, in this example 50 coats are needed to produce the target coating weight. In order to make this coating process more feasible as a production-level method, while maintaining control over the solvent and solvent-drug-polymer interaction, as just discussed, an efficient in-process drying step was needed.

Initial experiments configured a process to include a drying step using a divergent nozzle, which is what would normally be expected to remove a solvent. A cylindrical dryer nozzle was also used. Either of these nozzle types (cylindrical or diverging channel-type) were chosen as solutions.

A flow profile for the gas, i.e., a gas exit velocity from the nozzle and temperature, was selected to produce a rapid drying time. It was expected that with an appropriate average heat transfer from the gas to the stent surface using either nozzle, i.e., selecting a suitable drying gas velocity and temperature, an efficient in process drying stage could be incorporated into the coating process, thereby making feasible a process of applying many low weight coatings while maintaining control over the solvent's effects on the drug-polymer morphology. The resulting drug release profile resulting from the use of the diverging channel or cylindrical nozzle types for solvent removal, did not, however, exhibit the desired properties. It was hypothesized that more control over the heat transfer might be needed.

Surprisingly and unexpectedly, it was found that when the heat transfer capacity in the gas at the nozzle exit were modified, that is, made more uniform, there was significant improvement in the ability to control or tailor a drug release profile to suit the end objective. It was concluded, therefore, that not only is an efficient in-process drying step needed to produce an improved drug release profile, but also a more uniform heat transfer from the gas to the coated surface between each of several applied coatings.

In view of the foregoing, the invention provides one or more of the following improvements in the art.

According to one aspect there is a multi-step coating process that incorporates an in-process drying stage.

According to another aspect of invention, a method for coating a stent includes : (a) spraying the stent with a solution comprising about 2-5% coating by weight and 95-98% solvent by weight, (b) removing solvent from the coated stent using a heat nozzle such that following the removing solvent step only about 0.5% to 8% of the coating by weight is solvent remaining in the coating, and repeating steps (a) and (b) until 100% of a desired wet coating weight is reached.

Another aspect of the invention is a method for producing a desired release profile that includes a forced air drying stage for uniformly removing solvent.

Another aspect of invention was precise alignment of a stent with an exit nozzle. In one embodiment there is alignment tool or guide that places a stent body at an X, Y, and Z location determined to produce a uniform rate of solvent removal and uniform properties over the length of the stent body. In one embodiment the alignment error tolerance for an offset of a stent body from a nozzle tip (call it the "Z" direction) is higher than the tolerance for misalignments in the nozzle plane, e.g., within the plane of the paper in FIG. 4, which shall be called the X-Y plane. In one embodiment a bore site located proximal the nozzle allows precise alignment the stent body in the X-Y plane, e.g., a vertical laser groove 50 (FIG. 1A). According to one embodiment, unless the stent body is aligned properly there may be a significant loss in efficiency of drying and more non-uniformity of the evaporative drying process.

Another aspect of the invention is a heat nozzle that conditions a mass of pressurized gas for removing a low weight coating. The nozzle has a first and second tapered set of walls for accelerating and decelerating an upstream unconditioned gas stream. In other embodiments, the nozzle may have a first stage having a divergent taper, which decelerates a gas, and a second stage having a convergent taper, which accelerates a gas. The heat nozzle may further include a mixing screen.

Another aspect of the invention is a heat nozzle that that conditions a mass of pressurized gas for removing a low weight coating. The nozzle has a first and second diffuser section. One diffuser has a first set of apertures or holes and the second diffuser has a second set of apertures or holes, different from the first set.

Another aspect of the invention relates to producing a coating weight by applying a light layer, drying the layer and then repeating these steps several times until a total coating weight is achieved. The number of layers can be greater than 20, greater than 30, greater than 40, and between 20 and 50 layers.

Another aspect of the invention relates to a heat nozzle for use during an in-process drying step for coating a drug eluting stent. This heat nozzle may provide an air curtain with uniform velocity and temperature distribution, which improves the uniformity of solvent drying and reduces variability in drug release from the coating.

According to one aspect of the invention a drying nozzle having a mean flow direction, an inlet area that receives an incoming gas stream and an exit area that produces a drying gas, comprising: a chamber including a first side proximal the inlet and distal the exit, a second side distal the inlet and proximal the exit, and walls extending from the first side to the second side; the chamber walls defining an exit region, inlet region and mid-region of the nozzle, the exit region defining a first volume for gas flow from the mid-region to the nozzle exit, and the mid-region defining a second volume for gas flow from the inlet region to the exit region; the mid-region formed at least in part by walls that diverge way from each other in the flow direction and the exit region formed at least in part by walls that converge towards each other in the flow direction a first diffuser disposed proximal the inlet and distal the exit area, the first diffuser forming a first plurality of openings; a second diffuser disposed proximal the exit area and distal the first diffuser area, the second baffle forming a second plurality of openings and having a cross-sectional area configured to directed gas over the surface of a coated medical device, such that during steady state flow the nozzle produces a gas at the exit that has a substantially uniform velocity and temperature profile across the exit area.

According to another aspect of the invention, an apparatus for coating a stent includes a mandrel for holding the stent; a sprayer for applying a coating to a surface of the stent while it is being held on the mandrel; a dryer configured to remove a controlled percentage of solvent from a surface of the stent, the dryer including a nozzle and the nozzle forming a gas conditioning chamber.

The gas conditioning chamber includes an inlet receiving a heated gas provided from a gas source, a diverging section proximal the inlet and distal the exit, a converging section proximal the exit and distal the inlet, a first diffuser proximal the inlet and distal the exit, the first baffle having a first arrangement of openings, and a second diffuser proximal the exit and having a second arrangement of openings, wherein the inlet, diverging section, converging section and first and second diffusers cooperate to produce an accelerated, drying gas mass having a uniformly distributed capacity for heat transfer from the gas to the surface of the stent.

According to another aspect of the invention, a stent coating method includes the steps of applying a coating to the stent; and then drying the coated stent using a drying nozzle. The drying step includes the steps of disposing the coated stent proximal an exit of the nozzle; and at least partially removing a solvent in the coating with a gas forced through the nozzle, including the steps of decelerating the gas received through a nozzle inlet, the nozzle inlet being upstream of the exit, mixing the decelerated gas including forcing the gas through a first diffuser disposed proximal the inlet and distal the exit, accelerating the gas downstream of the first diffuser, and then forcing the accelerated gas through a second diffuser disposed at the exit to dry the stent; wherein the gas downstream of the exit has a substantially uniform temperature and velocity over the length of the stent.

According to another aspect of the invention there is a system including a spray station and drying station. The spraying and drying station may be separated by a wall. A stent is held on a mandrel that is supported as a cantilever or pin connection at its ends. First the stent is placed in a spray zone where a coating is applied. The stent is then moved to the drying zone where it is subjected to a uniform drying gas to provide an efficient and rapid drying. The stent is then moved back to the spray zone and the process repeated until a final coating weight is reached. In a preferred embodiment a dryer such as that illustrated in FIG. 1 is used. Other embodiments are possible in view of the disclosure.

The stent and mandrel supporting the stent is moved between the spray and drying zones by a means for moving between the sprayer and drying nozzle. In one embodiment the means is a rotary mechanism programmed to position a stent between a dryer and a nozzle section by coupling the mandrel to a rotating drum assembly. In another embodiment, a sprayer and nozzle are coupled to a linear motor that selectively positions the drying nozzle and spraying nozzle over the medical device when solvent is removed and a coat is applied, respectively.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIGS. 1A and 1B are perspective and front views, respectively, of a drying nozzle according to the disclosure. FIG. 1A illustrates a perspective view of a drying nozzle with a top cover removed to reveal the flow chamber within. FIG. 1B shows a front plan view of the nozzle, or the view in a plain perpendicular to the net direction of gas flow exiting the nozzle. This views shows a front profile of the exit end of the nozzle and the tapered sides forming the converging portions of the chamber.

FIGS. 2A and 2B illustrate a top and side views, respectively, of the nozzle of FIGS. 1A-1B and a stent disposed adjacent the exit end of the nozzle. These figures show the direction of flow into and exiting from the nozzle. The flow parameters of the drying gas at the exit of the nozzle are represented generally by the quantity g(v, t), where "v" and "t" represent the gas exit velocity and temperature, respectively, profile across the nozzle exit.

FIG. 3A-3C shows various views of a frame of the nozzle body of FIGS. 1-2. These figures illustrate the various relationships among flow regions for directing incoming gas toward the medical device.

Figure 4:
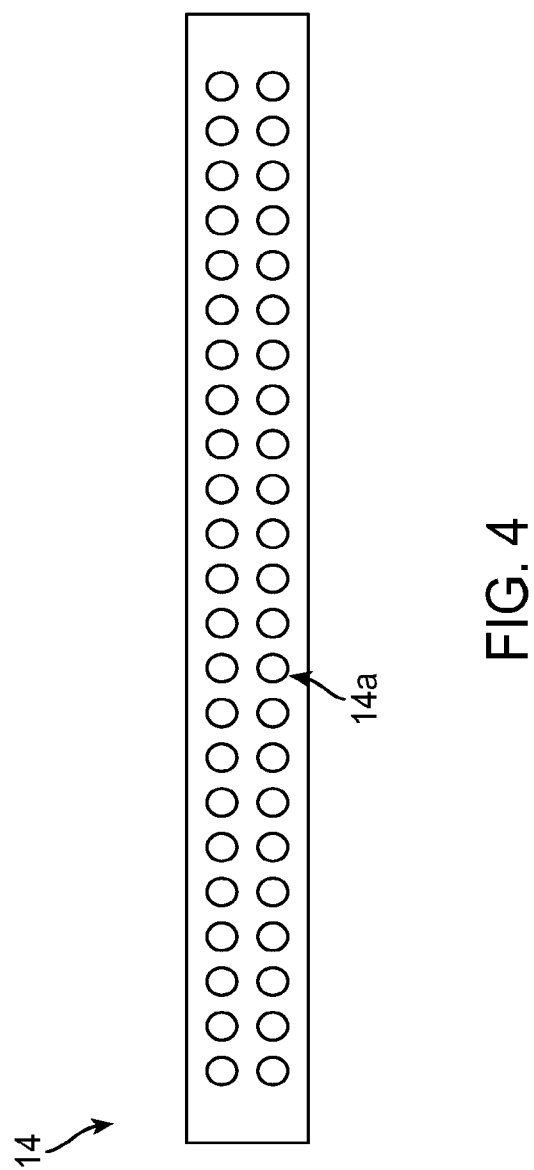
FIG. 4 shows a baffle of the nozzle of FIGS. 1-2.

11/764,006 (the '006 application) and U.S. application Ser. No. 12/027,947 (the '947 application).

DETAILED DESCRIPTION OF EMBODIMENTS

According to a preferred implementation of the invention, a sprayer and heat nozzle is used to form a drug-eluting coat on a surface of a stent. A stent is an intravascular prosthesis that is delivered and implanted within a patient's vasculature or other bodily cavities and lumens by a balloon catheter. The structure of a stent is typically composed of scaffolding, substrate, or base material that includes a pattern or network of interconnecting structural elements often referred to in the art as struts or bar arms. A stent typically has a plurality of cylindrical elements having a radial stiffness and struts connecting the cylindrical elements. Lengthwise the stent is supported mostly by only the flexural rigidity of slender-beam-like linking elements, which give the stent longitudinal flexibility. Examples of the structure and surface topology of medical devices such as a stent and catheter are disclosed by U.S. Pat. Nos. 4,733,665, 4,800,882, 4,886,062, 5,514,154, 5,569,295, and 5,507,768.

FIGS. 1-3 depict aspects of a drying nozzle 10 according to the disclosure. Referring to FIG. 1A, the nozzle 10 includes a downstream exit part 8 where a drying gas exits from holes formed in a baffle 14 and an upstream inlet part 16 connected to a pressurized gas source providing a heated, incoming gas stream. The nozzle 10 is shown in a partial exploded view (top cover 20 removed) to reveal an inner screen 32 (or screens 32) located within an inner flow chamber 30. The flow chamber 30 is formed by the assembly of a top cover 20, bottom cover 22, and frame 40 surrounding the chamber 30 portion upstream of the baffle 14. The frame 40 includes opposed, similarly shaped and tapered side walls. The frame 40 also forms, at a central location where the walls 41 and 42 meet, an inlet passage having a circular opening 43a (partially shown) through which the incoming gas stream enters the chamber 30. The frame 40 structure is shown in greater detail in FIGS. 3A-3C. A thermocouple 11 is attached to the top cover 20 to monitor the temperature of the gas within the chamber 30.

FIGS. 1B and 2A show top and front views of the nozzle 10, respectively. As explained in greater detail, below, the gas stream exiting from the baffle 14, denoted by the vector quantity g(v,t), will exit from the baffle with a substantially uniform velocity and temperature over the area defined as the product of length "L" and width "w" (FIG. 2A). This area denotes the area spanned by the arrangement of holes 14a of the baffle 14 through which the gas exits from the chamber 30.

The inlet gas having an input velocity $V_{in}$ is directed into the inlet end 16 in a flow direction through the circular aperture 43. The gas exiting, g(v,t), is also in the flow direction. A coated stent 5 having solvent to be removed by the gas g(v,t) is shown adjacent the exit 8 in FIGS. 2A and 2B. The stent 5 is aligned with the baffle 14 using a laser inscribed groove 50 that locates the centerline of the baffle with the longitudinal axis of the stent 5. According to one embodiment, the stent 5 is held by a mandrel that is moved with the stent between a coating station and the drying station where stent 5 is positioned beneath the baffle 14 as shown in FIG. 2. Alternatively, the stent 5 is stationary and the nozzle is moved into alignment with the stent 5. An alignment groove 50 may be provided to aid with this alignment. The stent and mandrel are rotated at a constant or intermittent rate as the nozzle applies heated gas to the stent surface 5.

The nozzle 10 converts the gas entering through the circular opening 43a into a mass of drying gas concentrated over a rectangular area matching the stent length and diameter. As such, the length and width of the arrangement of holes 14a in the baffle is relatively narrow and about the length of the stent 5. The drying gas may be thought of as a body having a thermal mass and dimensions projected over the rectangular area L×w. The body has a capacity to transfer heat or thermal energy to the coated stent surface uniformly through efficient conversion of laminar to turbulent fluid flow due to the nature of the nozzle design. For purposes of this discussion, the quantity g(v,t) may be thought of as a velocity and temperature profile, or as a heat transfer profile for the mass of gas exiting from the baffle 14.

FIGS. 2B and 1B show the sides of the nozzle 10. It can be seen that the sides formed by the top cover 20, bottom cover 22 and frame 40 walls 41 and 42 form a converging section terminating at the baffle 14. There are tapered sides for both the top and bottom sides forming the housing for the chamber 30.

During a steady state flow condition the laminar gas flux at the circular opening to chamber 30, denoted as 43a in FIG. 1A, is approximately the same as the turbulent gas flux at the exit 8 considering the compressibility factor to be minor. This "flux" refers to the rate of gas flow through a cross-sectional area perpendicular to the flow direction at any cross-sectional area in a flow region of the nozzle 10. The amount of gas per unit time passing through the area L×w of the baffle 14 is therefore the same as the gas per unit time passing through the circular opening 43a, or screen(s) 32 upstream of the nozzle exit 8. Consequently, at steady state the average velocity of the gas passing through the areas defined by these sections (or any other cross-section within the chamber 30) is inversely proportional to the respective cross-sectional areas through which the fluid passes. The smaller the cross-sectional area the higher the gas average velocity. The cross sectional areas referred to above are depicted in FIG. 3A by the quantities $A_i$, (inlet area), $A_e$ (exit area, i.e., the area L×w), and $A_s$ (i.e., the area where the screen(s) 32 are positioned in the chamber 30). The flux through each of these areas is approximately the same for steady state flow. The area $A_e$ is less than $A_i$. Thus, the gas velocity at the exit having area $A_e$ is higher than the gas velocity at the section having area $A_i$, because $A_e < A_i$.

Referring to top views of the frame 40 (FIGS. 3A and 3C) and a side view of the frame 40 (FIG. 3B), the frame 40 includes first opposed, diverging walls 41b and 42b located near the entrance opening 43a and upstream of the screen 32. Second opposed, converging walls 41a, 42a are located near the exit and downstream of the screen 32. Accordingly, it will be understood that for steady state flow gas entering chamber 30 from circular opening 43a will decelerate upstream of the screen 32 by diverging chamber walls and then accelerate by converging chamber walls downstream of the screen 32. The frame 40 includes notches 44a, 44b which hold the screen 32 in the chamber 30, and notches 45a, 45b which hold the baffle 14.

The taper for the walls 41a, 42a is denoted in FIG. 3C by the angle $\Theta_3$. And the taper for the walls 41b, 42b is denoted by the angle $\Theta_2$. Similarly, the taper for the top and bottom surfaces of the chamber 30, constant from the baffle 14 to the upstream rear wall 49a of the chamber 30 is denoted in FIG. 3B by angle $\Theta_1$.

Referring to FIG. 3B, which shows a side cross-sectional view taken at 3B-3B in FIG. 3A, the chamber 30 may be described as having three sections or regions of fluid flow. Flow region I refers to the inlet passage 43a (or opening 43a). This passageway is, according to one embodiment, a cylindrical bore that may be conveniently coupled at one end to a mating cylindrical pipe, which couples the nozzle 10 to the gas source. Region I ends at the chamber 30 entrance. The gas enters the chamber 30 by first entering flow region II. This region refers to the space formed by the diverging side walls 41b, 42b, top and bottom covers and the screen 32. Flow region III refers to the space in the chamber 30 downstream of the screen 32. This region is formed by converging side walls 41a, 42a, baffle 14, screen 32 and the top and bottom covers 20, 22. According to one embodiment the distance from the rear wall 49a to the screen 32 is substantially less than the distance from the screen 32 to the baffle 14. This relative sizing of regions II and III is depicted in FIG. 2.

The screen 32 held in groove 44 is suitably chosen to cause the decelerating gas entering the chamber 30 to form eddies, or induce turbulence. This produces a desirable mixing of the incoming and decelerating gas stream. In one embodiment, two screens are placed in groove 44. The first screen is a 500×500×0.0008" thick screen and a 10×10×0.025" thick second screen placed back to back. The region II may be thought of as a transition region from circular passage gas flow (region I) to rectangular passage gas flow (baffle 14), or the nozzle 10 mixing region.

Figure 5:
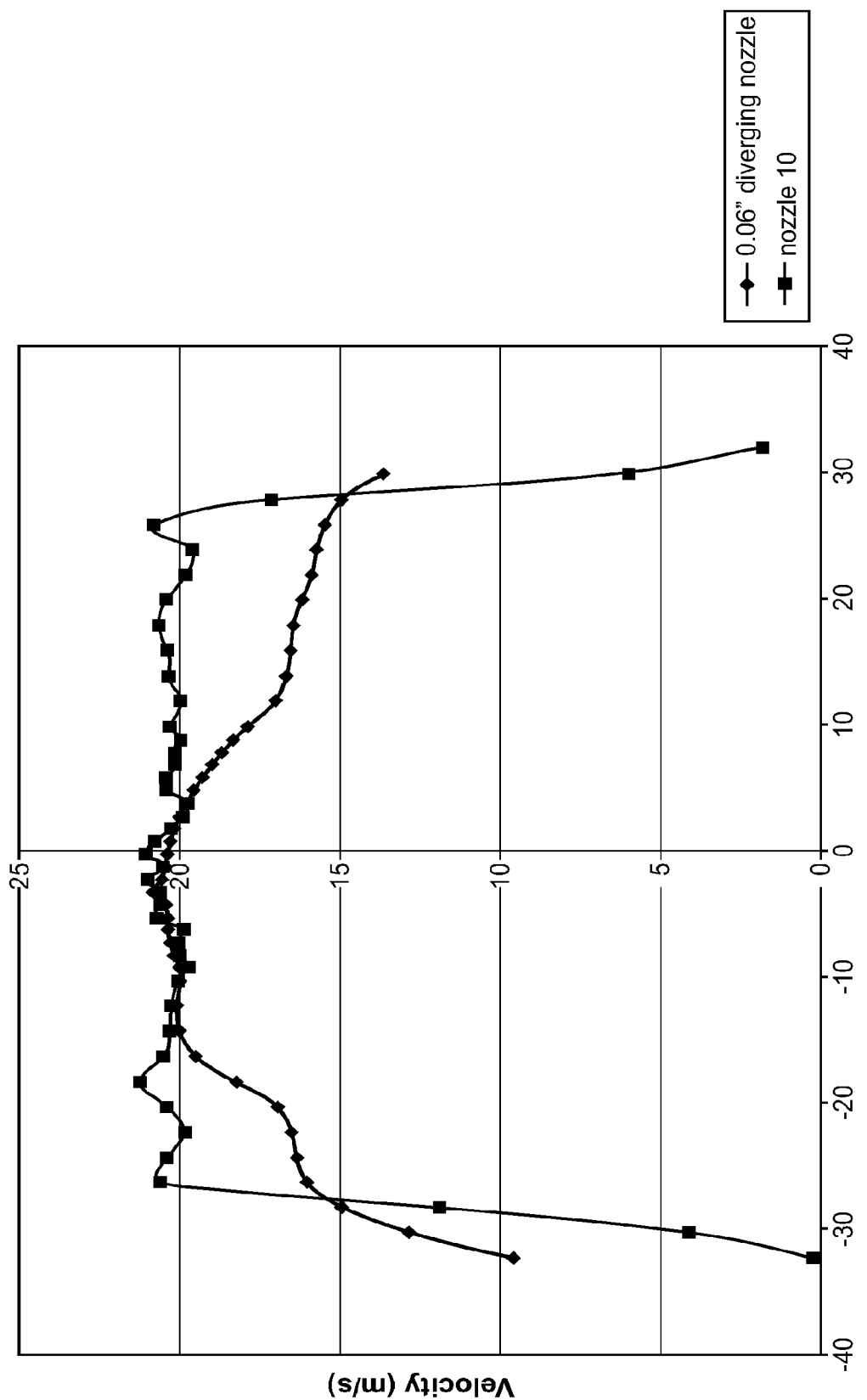
FIGS. 5-7 are plots showing the temperature and velocity distribution of gas at the nozzle exit for two types of nozzles.
Figure 6:
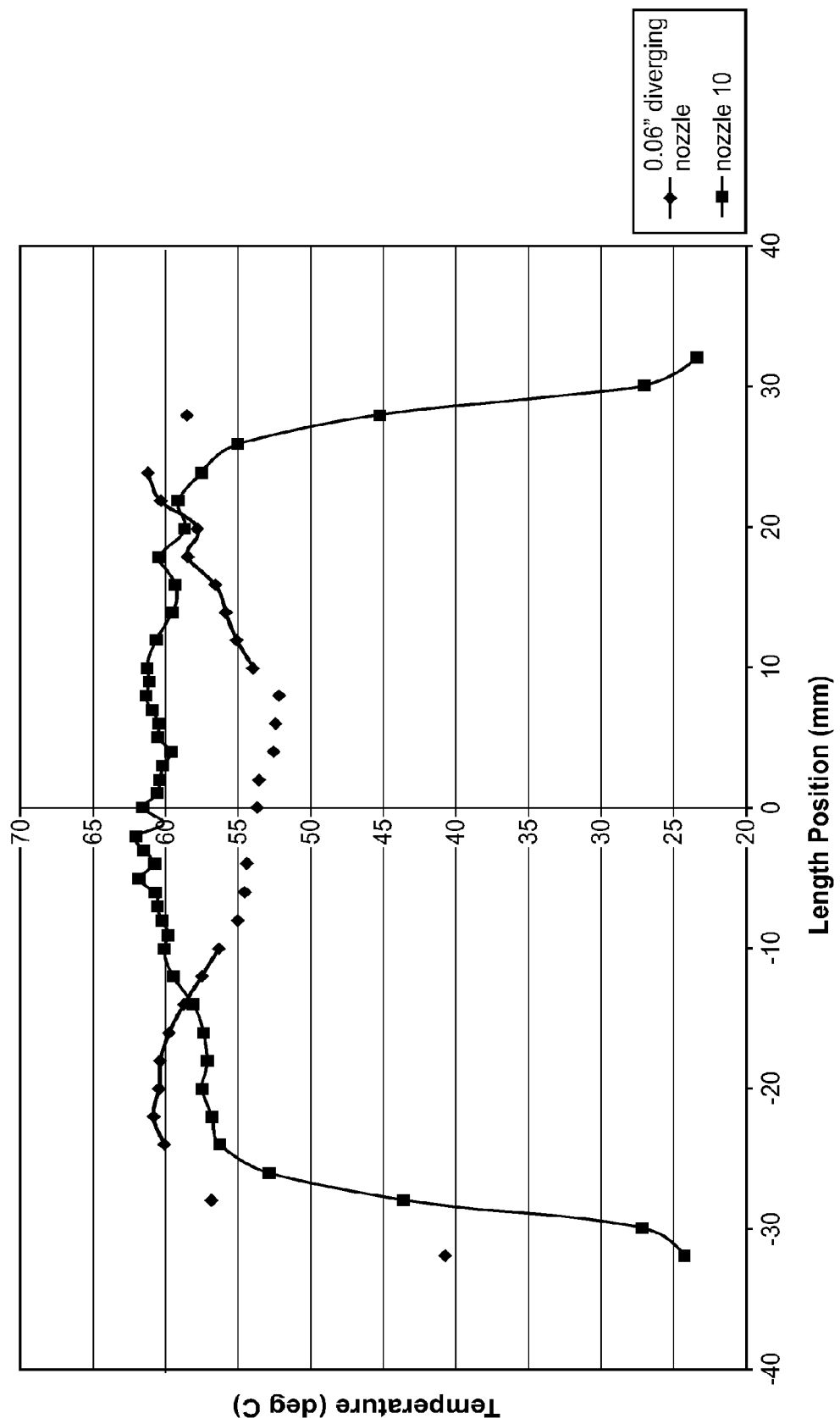

With the above assembly of the nozzle 10 the desired uniformity in flow properties and/or heat transfer capacity, i.e., uniform thermal mass and efficient drying, at the exit 8 was observed. The mass of gas exiting the baffle holes 14a had a more uniform velocity and temperature profile than the corresponding diverging channel having a 0.06" rectangular aperture at the exit (hereinafter the "0.06 nozzle"), as depicted in FIG. 5 (gas velocity verses distance from the center of the baffle) and FIG. 6 (gas temperature verses distance from the center of the baffle). The horizontal axis has as its zero position the center of the baffle. The distance +30 and −30 designates the ends of the arrangement of holes 14a, i.e., "L" in this case is 60 mm, for this example. This distance corresponds approximately to the length of the stent 5. As can be seen in the plots, the velocity and temperature profile are more uniform than in the case of the diverging nozzle having the 0.06" exit aperture.

The mixing of decelerating gas, reduction in stagnant gas upstream of the screen 32, and subsequent acceleration of a uniform thermal mass of gas downstream of the screen 32 is believed to have produced the favorable results. The diverging walls in region II decelerates the incoming gas, which enters through a circular opening. The walls are tapered outwardly (rather than forming corners or sides at right angles) to prevent stagnant gas from residing in region II. Stagnant gas buildup can effect the operating efficiency of the nozzle. The gas then mixes as it is forced through the mesh or screens 32. By placing the screen near the opening 43a, it is believed that greater mixing will occur. When the gas enters region III the converging walls accelerate the gas. The gas is then forced through the arrangement of holes in the baffle 14. The effect of the chamber 30 shape, placement of the screen 32 and baffle design 14 at the exit uniformly diffuses air between the circular inlet and rectangular exit, which produces the relatively high and uniform heat transfer capacity from the gas to the stent surface. The screens and baffle may be removable/interchangeable to allow for process-specific air flow patterns.

According to example, the gas outlet width (w) is 0.188 inches which is matched to the stent diameter that was dried with the nozzle. The baffle length (L) is 2.36 inches to provide a drying gas for stent lengths of 8 to 38 mm. An operating temperature of 25° C. to 110 ° C. (maximum temperature dependent on output of heater element and dimensional stability of nozzle base material) was chosen to accommodate drying of various solvents. The width of the baffle is, in some embodiments twice the outer diameter of the average stent dried using the nozzle. Baffle designs can be changed to produce a range of velocity profiles from the air outlet. A uniform velocity profile can be accomplished by utilizing a stainless steel mesh (preferable 150 to 500 squares per inch) in the screen 32 and a stainless steel machined lower baffle plate of uniformly spaced 0.060 inch holes.

According to one embodiment it was found that $\Theta_3$ greater than $\Theta_2$ and $\Theta_l$ (amount of taper, see FIGS. 3B and 3C) and the above screen and baffle selection produced the desired result. In particular, it was found that $\Theta_l$ about equal to 37 degrees, $\Theta_2$ about equal to 21 degrees and $\Theta_3$ about equal to 83 degrees, a screen section of 150 to 500 squares per inch and 0.06 inch baffle holes produced favorable results.

Figure 7:
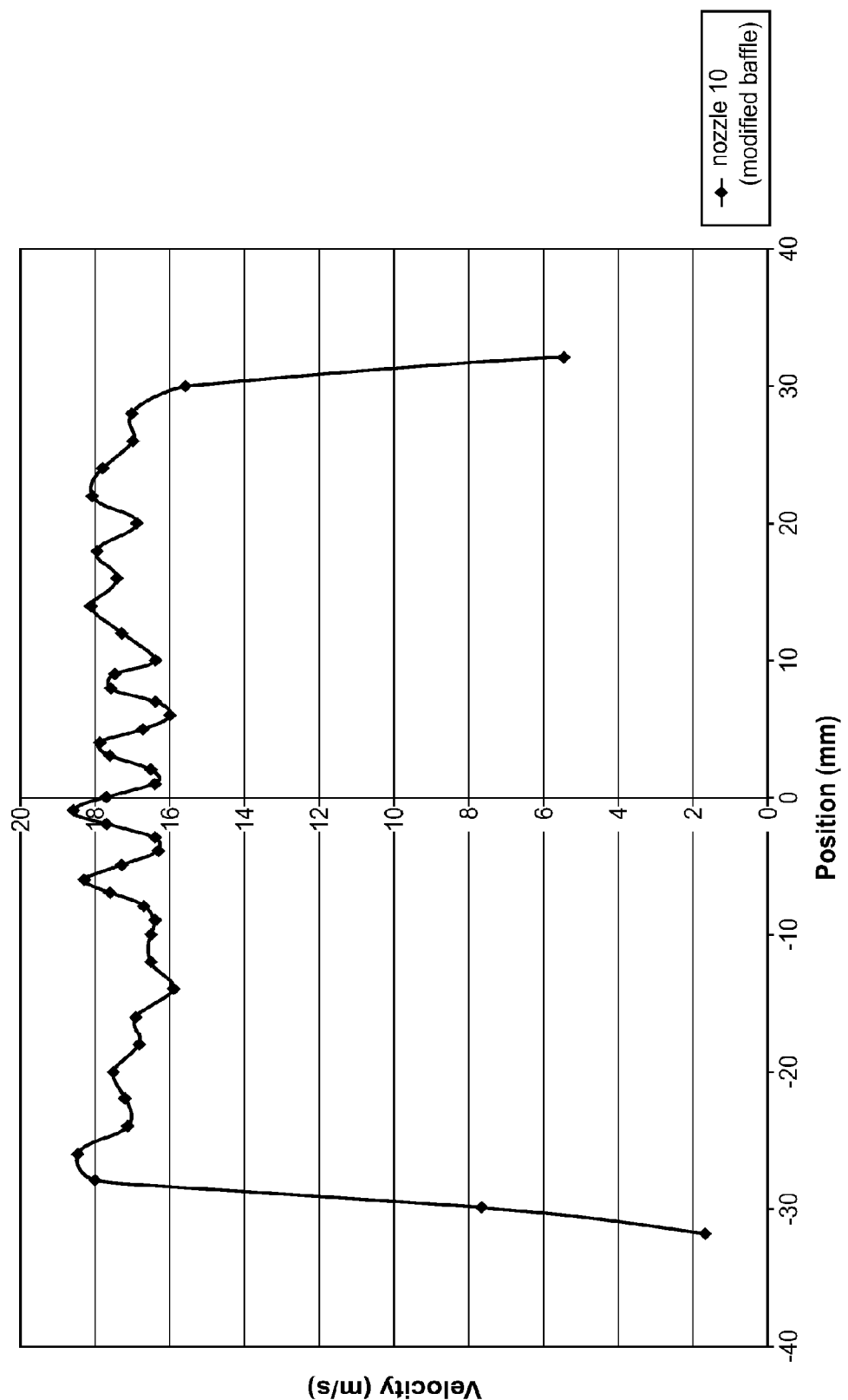

Different hole patterns or holes of varying diameter on the lower diffuser plate can also be utilized to create other velocity profiles (sinusoidal or sawtooth, linear gradient, velocity minima or maxima at centerpoint or stent ends) if controlled variation in drying rate is desired. FIG. 7 shows a somewhat sinusoidal velocity pattern formed by using an alternating 2-1-2 hole pattern on the baffle 14.

Coating experiments show an improved efficiency of drying and reduced variability in drug release rate using the nozzle according to the invention verses the diverging channel 0.06" nozzle. In-process coating weights were approximately 2% greater than final dry coating weights using the nozzle described above. More generally, for the in-process, or inter-pass drying stage the amount of solvent remaining (as a percentage of the total coating weight) can be between 0.5% to 8%, depending on the formulation of drug-polymer-solvent. This compares favorably to a 10% greater coating weight using the 0.06 inch nozzle (roughly 80% less solvent in the coating in-process). Drug release at 24 hours in vitro was observed to be less variable as well (relative standard deviation of approximately 10% versus 20% with a 0.06 inch nozzle). And stents coated using the nozzle 10 exhibited less mean shift in amount released (approximately 11% for the nozzle 10 compared to 39% with the 0.06 inch nozzle).

Embodiments of the present invention may be practiced using the spray coating devices described in U.S. application Ser. No. 11/764,006 (the '006 application) and U.S. application Ser. No. 12/027,947 (the '947 application).

Figure 8:
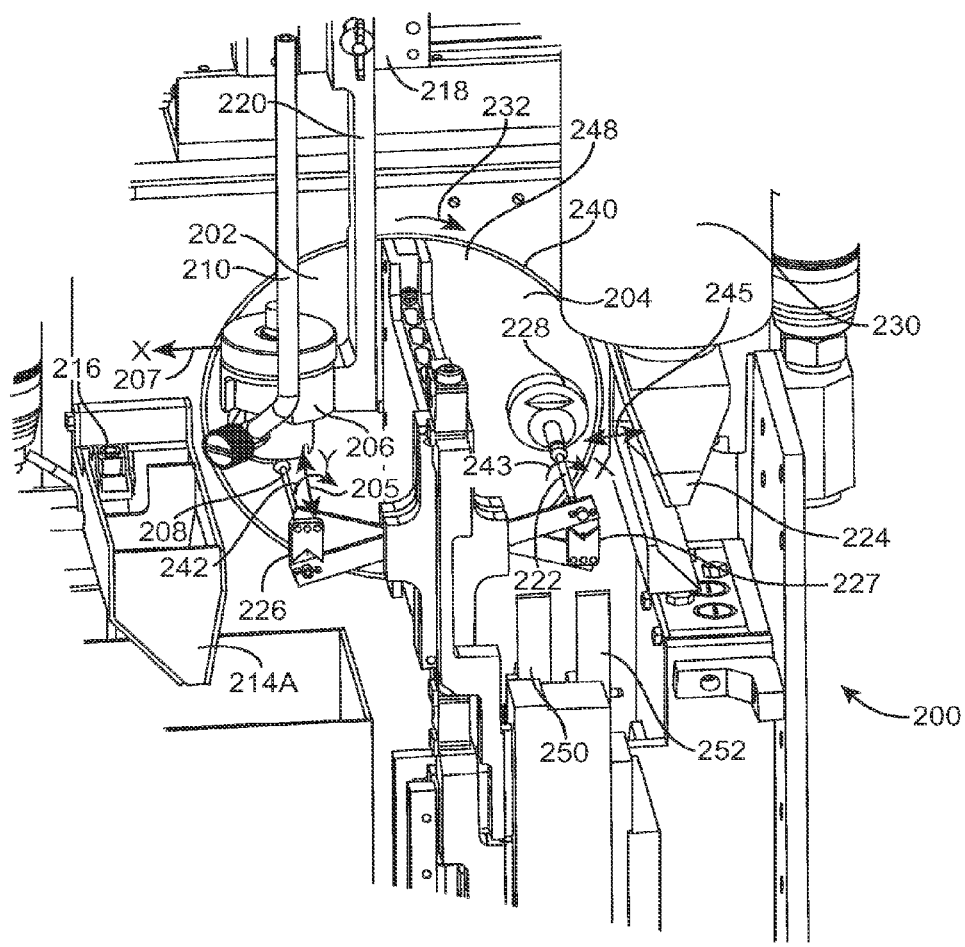
FIGS. 8, 9, 10A and 10B show various views of a nozzle and spraying—drying system incorporating aspects of the disclosure. Additional examples of a spraying system suitable for use with a heat nozzle constructed in accordance with the disclosure is found in U.S. application Ser. No.
Figure 9:
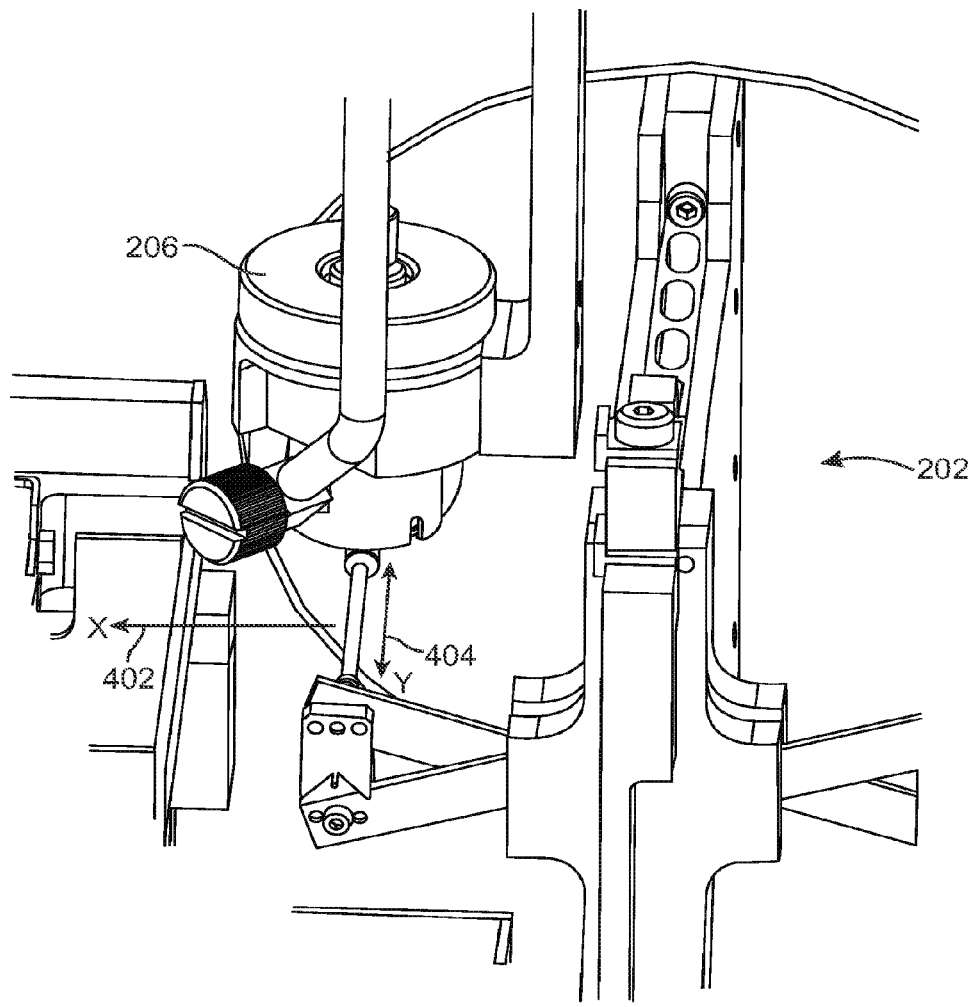
Figure 10A:
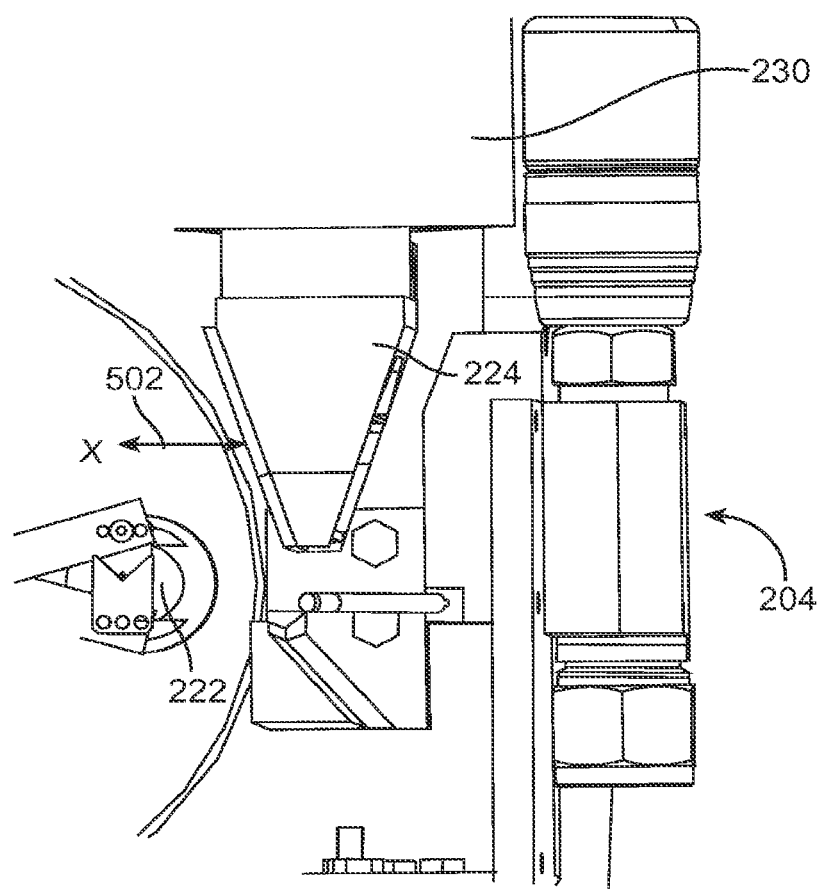
Figure 10B:
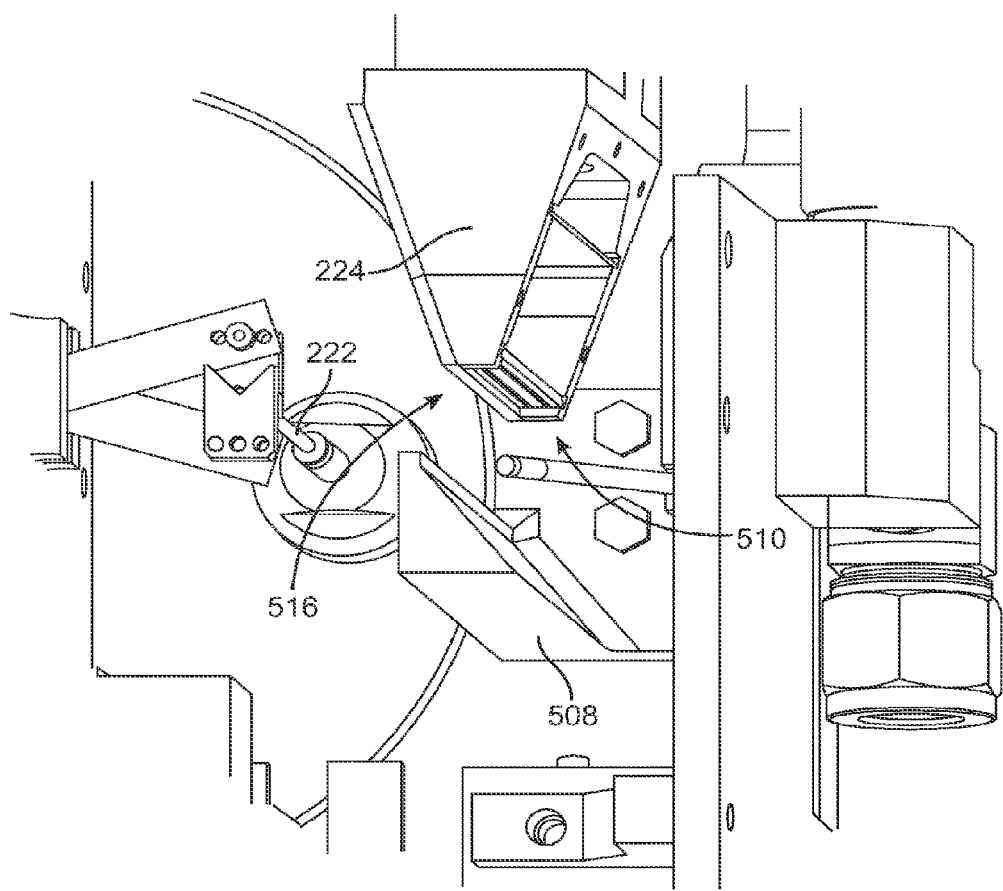

An example of a stent coating system incorporating some of the feature of the invention will now be described. Referring to FIGS. 8-10, a device 200 is configured to process two stents simultaneously. However, device 200 can process only one stent if desired. Device 200 has a spraying zone 202 and a drying zone 204, which enable coating of one stent and drying of another stent simultaneously. Stent support assemblies, mandrels 208 and 222 can be moved between spraying zone 202 and drying zone 204 via a rotating drum to allow simultaneous spraying of a stent on one stent support assembly and drying of another stent on another stent support assembly.

Spraying zone 202 has a spray nozzle 206 that is mounted above movable stent support assembly 208. As depicted by an arrow 242, stent support assembly 208 is rotated during the coating process. Spray nozzle 206 is translatable along a y-direction, as shown by double-headed arrow 205, along the axis of stent support assembly 208. Spray nozzle 206 is also movable along an x-direction as shown by an arrow 207.

Spray nozzle 206 is dwelled in a nozzle holder 220 which is attached to a mounting bracket block 218. Mounting bracket block 218 is coupled to a linear slide that can control movement of nozzle holder 220 and spray nozzle 206 back and forth in the x-direction during the application of the coating material over the stent. Mounting bracket block 218 is also coupled to a sliding stage to enable nozzle holder 220 along with spray nozzle 206 to side shift back and forth in the x-direction (245/207) to a position over upper funnel 214A after a spray cycle is complete. The side-shifting of nozzle holder 220 along with spray nozzle 206 clears the path in the spray zone to allow the drum 240 to rotate to advance the stent at the drying zone 204 to the spraying zone 202 to receive coating material.

Drying zone 204 includes a drying nozzle 224 constructed and operated in accordance with one or more the foregoing embodiments, e.g., nozzle 10. Nozzle 224 can be positioned over a movable mandrel assembly 222 for supporting a coated stent during drying. Mandrel assembly 222 is inserted into a spindle 228, which rotates the mandrel assembly 222 during the drying process, as indicated by an arrow 243. In some embodiments, the same motor may provide rotational motion to stent support assemblies 208 and 222. Drying nozzle 224 includes an electrical heater 230 to generate heated gas for drying nozzle 224. Drying nozzle 224 is movable and can shift in an x-direction, as shown by a double-headed arrow 245, or rotated (theta angle), from its position shown in FIG. 2 to a drying position over mandrel assembly 222. Drying nozzle 224 can be positioned above mandrel assembly 222 so that it can dry a stent coated in spraying zone 202 by blowing warm gas over a freshly coated stent. Stent grippers 250 and 252 for clocking a stent, as described in detail below, are disposed below mandrel assembly 222. Heater 230 is movable in the x-direction as indicated by 502 (see FIG. 10A).

Side shifting of drying nozzle 224 and spray nozzle 206 may be accomplished with pneumatic slides or motor driven linear slides. This side-shift allows the indexing drum to rotate, and can also accommodate differences in the drying time and the spraying time. The side-shift of drying nozzle 224 to a deflection plate 508 of the drying air away from the stent to prevent over-drying while the other stent is finishing its spray cycle.

Stent support assemblies 208 and 222 are supported at their distal ends by clamps 226 and 227, respectively. The proximal end of mandrel assembly 222 is shown supported by a spindle 228 in both the spray and dry zones. The proximal end of stent support assembly 208 is supported in the same manner, but is hidden by spray nozzle 206. The spindle 228 is mounted or coupled on a drum 240 which rotates as shown by arrow 232. Rotatable drum 240 can rotate to reverse the position of stent support assemblies 208 and 222 so that stent support assembly 208 is in drying zone 204 and mandrel assembly 222 is in the spray zone 202.

Referring again to FIG. 8, device 200 is designed to allow spraying of stent in spray zone 202 while a coating layer previously applied at spray zone 202 is dried at drying zone 204. Simultaneous spraying and drying reduces or eliminates idle time of sequential spraying and drying operation, thus increasing the throughput of a coating operation.

Specifically, a layer of coating material is applied to a first stent mounted on stent support assembly 208 by spray nozzle 206. At the same time, a second stent mounted on mandrel assembly 222 with coating material already applied in spray zone 202 is dried by drying nozzle 224. When both the spray coating on the first stent and drying of the second stent are completed, rotatable drum 240 rotates and positions the second stent (dried) at spray zone 202 and the first stent (freshly coated) at drying zone 204. The first stent may then be dried at drying zone 204 and a layer of coating material can be applied to the second stent at spray zone 202. The spraying and drying can be repeated a selected number of times as necessary to obtain a desired coating mass on each of the stents. Rotatable drum 240 can rotate clockwise or counterclockwise to change the position of the first stent and second stent between spray zone 202 and drying zone 204. Stent support assembly 208 and stent mandrel assembly 222 are rotated in each spraying and drying cycle. As shown by arrow 232, the first stent is rotated to spray zone 202 and the second stent is rotated to drying zone 204, and after the spraying/drying cycle is complete the first stent is rotated back to drying zone 204 for drying the stent and the second stent is rotated to spray zone 202 to receive coating material.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An apparatus for coating a stent including a drying nozzle having a mean flow direction, an inlet that receives an incoming gas stream and an exit that produces a drying gas, comprising:
   a mandrel for holding the stent;
   a sprayer for applying a coating to the stent; and
   the nozzle including
      a chamber including a first side proximal the inlet and distal the exit, a second side distal the inlet and proximal the exit, and walls extending from the first side to the second side;
      the walls defining an exit region, inlet region and mid-region of the nozzle, the exit region defining a first volume for gas flow from the mid-region to the exit, and the mid-region defining a second volume for gas flow from the inlet region to the exit region;
      the exit region formed at least in part by first wall portions that converge towards each other in the flow direction;
      a first diffuser disposed proximal the inlet and distal the exit, the first diffuser forming a first plurality of openings;
      a second diffuser disposed proximal the exit and distal the first diffuser, the second diffuser forming a second plurality of openings and having a cross-sectional area configured to direct gas over the surface of the stent,
      wherein during steady state flow the nozzle produces a gas at the exit that has a substantially uniform velocity and temperature profile across the stent.

2. The drying nozzle of claim 1, wherein the mid-region is formed by a circular opening in fluid communication with the inlet region, second wall portions that diverge in the flow direction, and the first diffuser.

3. The drying nozzle of claim 2, wherein the mid region is additionally formed by third wall portions that converge in the flow direction.

4. The drying nozzle of claim 1, wherein the exit region extends from the first diffuser to the second diffuser.

5. The drying nozzle of claim 4, wherein the mid-region has a length measured in the flow direction that is less than a length of the exit region measured in the flow direction.

6. The drying nozzle of claim 1, wherein the inlet region is formed by a cylindrical bore and the exit region forms a rectangular passage proximal the exit, the rectangular passage having a height and length to match a length and diameter of the stent.

7. The drying nozzle of claim 6, wherein the second diffuser has an arrangement of holes having a size of about 0.06 inches.

8. The drying nozzle of claim 7, wherein the first diffuser includes a first and second screen, wherein one of the screen sizes is between 150 and 500 squares per inch.

9. A stent coating method, comprising the steps of:
   (a) applying a coating to a stent, wherein the applied coating is at most a percentage of a total coating weight selected from the set consisting of 0.5% of the total coating weight, 2% of the total coating weight, 5% of the total coating weight and 10% of the total coating weight;
   (b) after applying the percentage of the total coating weight, at least partially drying the stent using the apparatus of claim 1;
   (c) repeating steps (a) and (b) until the total coating weight is reached.

\* \* \* \* \*